United States Patent [19]

Robert-Guroff et al.

[11] Patent Number: 4,755,457
[45] Date of Patent: Jul. 5, 1988

[54] METHOD FOR DETECTING HTLV-III NEUTRALIZING ANTIBODIES IN SERA

[76] Inventors: Marjorie Robert-Guroff, 6116 Tilden La., Rockville, Md. 20852; Robert C. Gallo, 8513 Thornden Ter., Bethesda, Md. 20817

[21] Appl. No.: 40,748

[22] Filed: Apr. 20, 1987

Related U.S. Application Data

[63] Continuation of Ser. No. 698,588, Feb. 5, 1985, abandoned.

[51] Int. Cl.$^4$ ................. G01N 33/569; G01N 33/564; C12Q 1/70
[52] U.S. Cl. ........................................... 435/5; 435/7; 435/29; 435/32; 435/240.2; 435/948; 436/506; 436/510
[58] Field of Search ............... 435/5, 7, 29, 68, 172.2, 435/32, 240.2, 240.27, 948; 436/506, 510; 530/387

[56] References Cited

U.S. PATENT DOCUMENTS

4,520,113  5/1985  Gallo et al. ............................. 435/5

OTHER PUBLICATIONS

Robert–Guroff, M. et al., Nature 316:72–74 (Jul. 1985).
Harada, S. et al., Science:229:563–566 (Aug. 1985).
Groopman, J. E. et al., Nature 316:12 (Jul. 1985).
Weiss, R. A. et al., Nature 316:69–72 (Jul. 1985).
McDougal, J. S. et al., J. Immunoloical Methods, 76(1):171–184 (1985).
Nagy, J. et al., Magy. Onbol. 29(1):11–18 (1985), cited in Bio. Abstract No. 80036659.
Shaw, G. M. et al., Science 226:1165–1171 (Dec. 1984).
Ho, D. D. et al., Proc. Natl. Acad. Sci., U.S.A., 81:7588–7590 (Dec. 1984).
Laurence, J. et al., New Engl. J. Med., 311(20):1270–1271 (Nov. 1984).
Zagury, D. et al., Science 226:449–451 (Oct. 1984).
Ho, D. D. et al., Science 226:451–453 (Oct. 1984).
Mitsurja, H. et al., Science 226: 172–174 (Oct. 1984).
Montagnier, L. et al., *Human T–Cell Leukemia/Lymphoma Virus,* Cold Spring Harbor Laboratory (1984), Gallo R. C et al., eds., CSH, N.Y., meeting date (Sep. 1984).
Levy, J. A. et al., Science 225:840–842 (Aug. 1984).
Montelaro, R. C. et al., J. Biol. Chem. 259(16):10539–10544, (Aug. 1984).
Popovic, M. et al., Science 224:497–500 (May 1984).
Vilmer, E. et al., The Lancet 7(8380):753–757 (4–1984).
Barré-Siroussi, F. et al., Science 220:868–870 (May 1983).
Altaner, C., Biol. Listy. 48(2):120–133 (1983), cited in Bio. Abstract 78084652.
Klatzmann, D. et al., Nature 312:767–768 (12–1984).
Dalgleish, A. G. et al., Nature 312:763–767 (12–1984).
Claphman, P. et al., Proc. Natl. Acad. Sci., U.S.A. 81(9): 2886–2889 (1984), cited in Bio. Abstract 78060777.
Davis, B. D. et al., *Microbiology,* 3rd Ed., Harper & Row, Philadelphia, (1980), pp. 1018–1030.
Clapham, P. et al., Science 222:1125–1127 (12–1983).
Nagy, K. et al., Int. J. Cancer 32:321–328 (1983).

*Primary Examiner*—Margaret Moskowitz

[57] ABSTRACT

This invention relates to a method to measure natural human antibodies in sera which will neutralize HTLV-III infection in an in vitro assay. Basically, cell-free virus is incubated with serum and used to infect H9 cells, which are then put in culture for three days, and viral infectivity is assayed using a monoclonal antibody specific for HTLV-III p24 in an immune fluorescent assay.

1 Claim, 1 Drawing Sheet

METHOD FOR DETECTING HTLV-III NEUTRALIZING ANTIBODIES IN SERA

This application is a continuation of application Ser. No. 06/698,588, filed Feb. 5, 1985, now abandoned.

BACKGROUND

During the recent past in 1984 the virus HTLV-III emerged as the most probable causative agent of acquired immune deficiency syndrome (AIDS) illness (see Gallo, et al, in the Material Information Disclosure, post 1, 2, 3). Also when an H9 cell is suitably infected with the HTLV-III virus and cultivated, an immortalized product results. The HTLV p24 core antigen has been isolated and purified from the immortalized H9/HTLV-III cell line (Gallo, et al, Ser. No. 635,610 filed July 30, 1984, now abandoned, "Isolation of p24 Core Protein of HTLV-III).

GENERALIZED PROCESS

In the present invention the natural antibodies in sera are assessed for their ability to neutralize HTLV-III infection. HTLV-III infection is monitored by following expression of the viral core protein, p24, by means of a specific monoclonal antibody to HTLV-III p24.

Also in the present invention the effect is to use sera with accompanying antibodies within it to effectively neutralize an amount of virus. This antibody neutralization may be either in whole or in part and a quantitative estimate of neutralizing antibody titer may be made using the outlined procedures. The method is applicable to serum from any species and hence is useful for assessing potential vaccine preparations for effectiveness in eliciting an HTLV-III neutralizing antibody response. In the last step, when it is not possible to observe viral infection within three days, then the serum has neutralized the viral infectivity in toto. It is believed that the neutralizing antibody in the sera bind to the viral envelope glycoprotein which is responsible for the intitial attachment of the virus to the receptors and, thus, blocks the infective action of the virus.

Also, the effort is made to utilize for a special purpose assays for HTLV-III dependent on antigen-antibody reaction and the presence of antibodies in sera of AIDS and related patients which neutralize viral antigen and are useful for protection.

Sketch I shows the process of the present invention.

---
Sketch I
---
Virus (HTLV-III) +
Serum (with or without neutralizing antibodies)
↓ Binding of specific antibody to viral antigen
Infect H9 cells and cultivate (3 day hold)
↓
Assay for virus infectivity by monitoring expression of HTLV-III p24
---

MATERIAL INFORMATION DISCLOSURE (1) Sarngadharan, et al, "Antibodies Reactive with Human T-lymphotropic Retroviruses (HTLV-III) in the Serum of Patients with AIDS," *Science*, 224:506-508, 1984.

(2) Safai, et al, "Seroepidemiological Studies of Human T-lymphotropic Retrovirus Type III in Acquired Immunodeficiency Syndrome," *Lancet*, i, 1438-1440, 1984.

(3) Gazzolo, et al, "Antibodies to HTLV-III in Haitian Immigrants in French Guiana," *New Engl. J. Med.*, 311:1252-1253, 1984.

(4) Clumeck, et al, "Seroepidemiological Studies of HTLV-III Antibody Prevalence Among Selected Groups of Heterosexual Africans," to be presented at the International Conference on AIDS, Atlanta, Apr. 14-17, 1985.

(5) Gonda, et al, "Sequence Homology and Morphologic Similarity of the AIDS Virus, Human T-cell Lymphotropic Virus Type III (HTLV-III), and Visna Virus, a Member of the Pathogenic Lentivirus Subfamily," *Science*, in press.

(6) Robert-Guroff, et al., "Detection of the Human T-cell Lymphoma Virus p19 in Cells of Some Patients With Cutaneous T-cell Lymphoma and Leukemia Using a Monoclonal Antibody," *J. Exp. Med.*, 154:1957-1964, 1981.

(7) U.S. Ser. No. 635,610, Gallo, et al, filed July 30, 1984, "Isolation of p24 Core Protein of HTLV-III."

None of the above references disclose the present method for detecting natural antibodies in sera which neutralize HTLV-III and protect therefor and measure the residual viral infectivity with a specific MAB such as anti-p24 HTLV-III (BT3 Biotech Research Labs, Veronese et al submitted).

THE INVENTION

The isolation of the human T-cell leukemia (lymphotropic) virus type III (HTLV-III) from cells of numerous patients with the acquired immunodeficiency syndrome (AIDS) presented the first evidence that the virus was the etiologic agent of the disease. This conclusion has been strengthened by the results of many subsequent investigations including those of seroepidemiologic studies which showed the presence of HTLV-III specific antibodies in the serum of the vast majority of patients with AIDS and AIDS-related complex (ARC). In addition, viral specific antibodies have been found in the serum of every group originally identified as at risk for AIDS, including homosexual males, hemophiliac recipients of factor VIII, intravenous drug users, and Haitians. More recent and wide-ranging serologic studies have identified additional populations exposed to the virus including heterosexual partners of AIDS or ARC patients and individuals from certain regions of Africa, especially Zaire and Rwanda, where AIDS as well as HTLV-III appear to be endemic.

While these sero-epidemiologic studies have provided many insights into the mode of transmission and extent of HTLV-III infection, there have been no reports concerning possible protective or therapeutic effects of HTLV-III specific antibodies in sero-positive individuals. Therefore an investigation was conducted to determine if AIDS and ARC patients possess antibody activities capable of inhibiting viral infection. Such a natural defense mechanism enables an infected host to avoid cell to cell spread of the virus and, hence, progression of the disease may be retarded or prevented. In several animal retroviral systems, neutralizing antibodies have been described which bind to the viral envelope glycoprotein which is responsible for initial attachment of the virus to the target cell receptor (Steeves, R. A., et al, *J. Virol.*, 14:187-189, 1974). By blocking the binding of virus to this receptor, virus neutralizing antibodies may effectively inhibit viral infection. In the studies reported here, it was asked whether HTLV-III elicited specific neutralizing antibodies in AIDS or ARC patients and whether any protective effect of such antibodies could be demonstrated.

The H9 clone of the HT cell line (specific process and examples) was used as target for cell-free HTLV-III infection, and several sera were initially analyzed for virus neutralizing antibody activity. Infection of the H9 cells was assessed by monitoring the expression of HTLV-III p24 using a monoclonal antibody in an indirect immune fluorescence assay. FIG. 1 illustrates the kinetics of infection of H9 cells with HTLV-III virus preincubated with sera positive or negative for virus neutralizing activity. By three days post-infection, approximately 80% of the H9 cells incubated with HTLV-III pretreated with serum of a healthy normal donor were infected as indicated by their expression of HTLV-III p24. In contrast, only 10% of H9 cells expressed HTLV-III p24 at day three when infected with virus pretreated with serum from a patient with ARC. That this inhibition of infection was mediated by a viral rather than a cellular antigen was shown by ready infection of H9 cells with HTLV-III following pre-treatment of the cells rather than the virus with the same sera (FIG. 1a). The inhibitory activity of certain sera was not simply a non-specific effect of high serum concentrations because the activity was titratable. As illustrated by the several sera titrated in FIG. 1b, sera possession inhibitory activity were found in all categories of patients and healthy members of groups at risk for AIDS.

In order to confirm that the inhibitory activity detected was directed against a viral rather than a cellular antigen, sera were absorbed with preparations of cell-free virus or with infected or uninfected H9 cells. While absorption with cells had little effect, absorption with viral preparations substantially decreased titers of sera with inhibitory activity as shown in Table 1 below.

Natural antibodies capable of neutralizing HTLV-III infection of H9 cells were detected in 60% of adult AIDS patients and in 80% of adults with ARC, but in 0% of normal healthy heterosexual controls. Geometric mean antibody titers were two-fold higher in ARC patients compared to AIDS patients and were even higher in 2 antibody positive healthy homosexuals. This finding suggests that virus neutralizing antibodies may exert some in vivo protective effect. The presence of these antibodies indicates an immunologic response to HTLV-III which may be utilized for therapeutic advantage. Also, the methodology employed in these studies can be directly useful in monitoring future vaccine approaches.

Therefore, having defined a system in which serum IgG could neutralize the infectivity of HTLV-III for H9 cells by binding to the virus, a number of human sera were analyzed for this antibody activity. The results are summarized in Table 2 below. It is clear that a high prevalence of patients with either AIDS or ARC possess virus neutralizing antibodies in contrast to healthy heterosexual individuals in which no such activity was demonstrated. While antibody titers ranged upwards of 500 for both patient groups, overall titers were low. However, it was observed that ARC patients possessed a two-fold higher geometric mean antibody titer compared to that of the AIDS patients studied. It was also seen that among healthy homosexuals at risk for development of AIDS, the geometric mean antibody titer, albeit determined on only 2 antibody positive individuals, was substantially higher than that of either of the two patient groups. This trend of higher titer with less or insignificant disease manifestations suggests a protective effect of the neutralizing antibodies.

HTLV-III neutralizing antibody activity was not detected in any normal healthy heterosexual individuals (Table 2). However, a barely detectable titer (of 13) was obtained in one of 4 serum samples from patients with acute mononucleosis. This result may suggest some weak cross-reactivity with viral antigen in sera possessing high levels of heterophilic antibodies.

In other retroviral systems, the major envelope glycoprotein is the target for neutralizing antibody. These naturally occurring virus neutralizing antibodies may be meaningful with regard to an in vivo protective effect.

The results of the present invention show a trend that individuals with less severe disease or those infected with HTLV-III but not yet manifesting clinical symptoms, possess higher neutralizing antibody titers. This suggests a human vaccine approach may be worthwhile. On the other hand, it is interesting to speculate that the role of neutralizing antibody in the overall biology of HTLV-III may be similar to that found in the visna virus system. Infection with visna virus, a non-oncogenic retrovirus which causes a slowly progressive disease in sheep affecting primarily the lungs and central nervous system, is persistent. It has been shown that neutralizing antibodies elicited by the virus have a narrow range of specificity which cannot inhibit infection by mutant viruses which arise during the course of the disease. Thus, the neutralizing antibodies exert a selective pressure, leading to replication of non-neutralized mutant viruses. It is also of interest that "early sera" taken from relatively recently infected animals possess a more restricted neutralization range compared to "late sera" obtained from animals infected for more than three years. These "late sera" were able to neutralize a broader range of visna mutants including all ancestral strains. This is relevant to HTLV-III especially because of the demonstrated genomic variability from isolate to isolate, particularly in the viral envelope region and also because of the demonstrated relatedness of HTLV-III to visna virus (Gonda, et al, *Science*, in press).

The demonstration of HTLV-III neutralizing antibodies in sera of patients with AIDS and ARC and in healthy individuals infected with HTLV-III is a meaningful finding which demonstrates an immunologic response during the course of disease development which may be utilized for therapeutic advantage. It furthermore indicates that appropriate vaccine approaches may be effective in preventing viral infection from the outset. The methodology described here will be useful in monitoring these future procedures and will also be useful in additional basic investigations concerning the biology of HTLV-III infection. Further studies will determine whether the presence of virus neutralizing antibodies in patient sera have any prognostic value or will be indicative of appropriate treatment regimens.

DESCRIPTION OF THE FIGURES

Sera from a normal healthy heterosexual (O) and from a patient with ARC (●) are compared in FIG. 1A. In a parallel experiment, these same sera were preincubated with H9 cells for 1 hr at 4° C. The cells were washed with PBS, incubated with the cell-free HTLV-III preparation, and cultured as in Example 2. Results of this treatment of the H9 cells with sera are represented for the normal, healthy heterosexual serum (Δ) and the serum of the patient with ARC (▲).

EXAMPLE 1

Figure 1B:
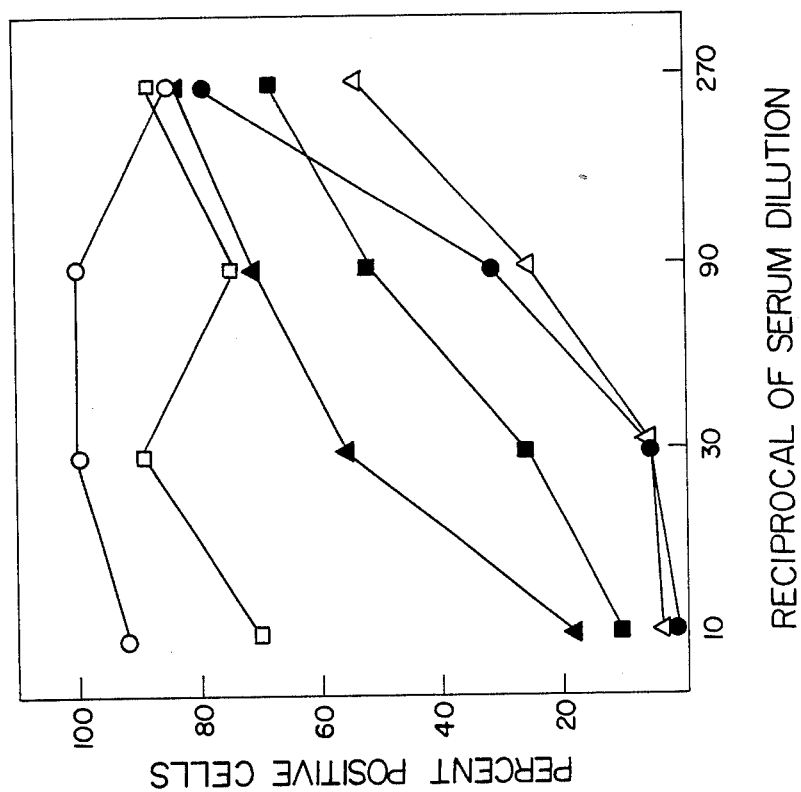
In FIG. 1B representative titrations are shown for two sera negative for viral neutralizing antibody activity: a patient with AIDS (O) and a patient with ARC (□). Representative sera positive for virus neutralizing antibody were obtained from a pediatric AIDS case (●), a patient with ARC (■), a healthy homosexual (Δ), and an adult AIDS patient (▲). All values obtained were normalized to the level of infection attained in the presence of a standard antibody-negative serum.
Figure 1A:
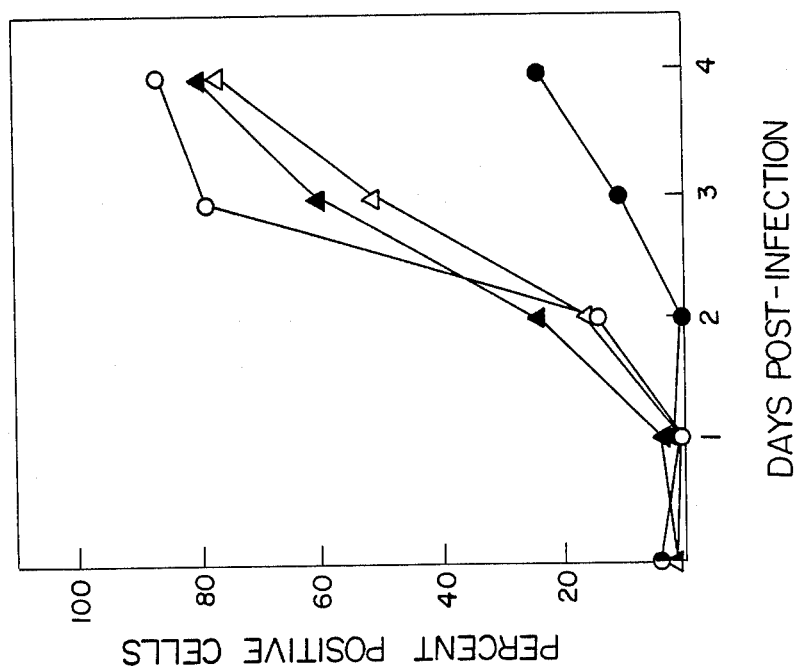

For virus absorption experiments, 62 ml of cell-free virus supernatant containing 2 to $5 \times 10^8$ virus particles/ml were pelleted as described in FIG. 1. The viral pellet was resuspended in 100 ul of a 1:10 dilution of serum to be absorbed and incubated overnight at 4° C. The virus was again pelleted by centrifugation and the absorbed serum was saved for titration of virus neutralizing antibody activity. Sera were similarly absorbed on pellets of washed $10^7$ cells and titered.

TABLE 1

HTLV-III Neutralizing Activity is a Property of IgG and is Directed Against a Viral Antigen

| Serum Sample | Patient Diagnosis | Serum Treatment (a) | HTLV-III Neutralizing Antibody Titer (b) |
|---|---|---|---|
|  |  | Experiments with Purified IgG: |  |
| 1 | ARC | None | 115 |
|  |  | Purification of IgG | 110 |
| 2 | AIDS | None | 34 |
|  |  | Purification of IgG | 40 |
| 3 | ARC | None | 60 |
|  |  | Purification of IgG | 76 |
|  |  | Absorbtion Experiments: |  |
| 4 | ARC | None | 135 |
|  |  | Absorbed with HTLV-III | <10 |
|  |  | Absorbed with H9 Cells | 120 |
|  |  | Absorbed with H9/HTLV-III | 90 |
| 5 | AIDS | None | 75 |
|  |  | Absorbed with HTLV-III | <10 |
|  |  | Absorbed with H9 cells | 22 |
|  |  | Absorbed with H9/HTLV-III | 34 |
| 6 | ARC | None | >270 |
|  |  | Absorbed with HTLV-III | 50 |
|  |  | Absorbed with H9 cells | >270 |
|  |  | Absorbed with H9/HTLV-III | >270 |

AIDS = acquired immunodeficiency syndrome
ARC = AIDS related complex
(a) IgG was purified from 0.5 ml aliquots of human serum by absorption to protein A-Sepharose equilibrated in PBS. Following extensive washing of the columns with PBS, IgG was eluted with 0.1 M glycine-HCl, pH 2.8. The eluate was neutralized with 2 M Tris-HCl, pH 8.0, dialyzed extensively against 10 mM ammonium bicarbonate, and lyophilized. The purified fractions were dissolved in 0.5 ml PBS, filter sterilized, and diluted in media for titration of neutralizing antibody activity as described in Example 2.
For virus absorption experiments, 62 ml of cell-free virus supernatant containing 2 to $5 \times 10^8$ virus particles/ml were pelleted as described in Example 2. The viral pellet was resuspended in 100 ul of a 1:10 dilution of serum to be absorbed and incubated overnight at 4° C. The virus was again pelleted by centrifugation and the absorbed serum was saved for titration of virus neutralizing antibody activity. Sera were similarly absorbed on pellets of washed $10^7$ cells and titered.
(b) Values for percent of HTLV-III p24-positive cells were normalized to the level of infection obtained in the presence of a standard negative serum treated similarly as the test serum. Antibody titers were then expressed as the reciprocal of the serum dilution at which virus infection was 60% of that obtained in the presence of this standard negative serum.

TABLE 2

HTLV-III Neutralizing Antibody in AIDS and ARC Patients and Others at Risk[a]

| Serum Source | No. Positive No. Tested | Percent Positive | Range of Titer | Geometric Mean Titer |
|---|---|---|---|---|
| Adult AIDS Patients | 21/35 | 60 | 10–520 | 44 |
| Pediatric AIDS Patients | 9/9 | 33 | 80–180 | 117 |
| Adult ARC Patients | 28/35 | 80 | 17–560 | 88 |
| Healthy Homosexuals | 2/12 | 17 | 130–340 | 210 |
| Healthy Heterosexuals | 0/20 | 0 | — | — |
| Heterosexual Partners of AIDS Patients[b] | 1/3 | 33 | 78 | — |
| Mothers of Pediatric AIDS Patients[c] | 0/2 | 0 | — | — |
| Siblings of AIDS Patients[d] | 1/2 | 50 | 55 | — |
| Patients with Acute Mononucleosis | 1/4 | 25 | 13 | — |
| Patient with Sarcoidosis | 0/1 | 0 | — | — |

AIDS = acquired immunodeficiency syndrome; ARC = AIDS related complex
[a] All sera were screened for virus neutralizing antibody at a 1:10 dilution. Those sera possessing activity were further titered as described in Example 2. Antibody titer is defined in the footnote to Table 1.
[b] All 3 individuals were positive for HTLV-III antibodies by the ELISA and Western blot assays.
[c] Sera from these 2 foster mothers were negative for HTLV-III antibodies by the ELISA and Western blot assays.
[d] The positive sibling was also antibody positive by the ELISA and Western blot assays.

Values for percent of HTLV-III p24-positive cells were normalized to the level of infection obtained in the presence of a standard negative serum. Antibody titers were then expressed as the reciprocal of the serum dilution at which virus infection was 60% of that obtained in the presence of a standard negative serum.

EXAMPLE 2

In the method for screening human sera for HTLV-III neutralizing antibodies, media containing 2 to $5 \times 10^8$ HTLV-III particles/ml were harvested from H9/HTLV-III cells. The amount of virus initially used was determined by titrating a virus preparation and selecting an amount for the assay which would achieve 50 to 80% of infected H9 cells by 3 days post infection. This in general required a substantial excess of virus particles per target cell. Cells were removed by low-speed centrifugation and the virus-containing supernatant was centrifuged for 3 hours at 32,000 x g. The viral pellets were resuspended in a total volume of 2.25 ml media (RPMI 1640 containing 20% fetal calf serum and penicillin/streptomycin). Uninfected H9 cells were washed in media and incubated for 20 minutes at room temperature in media containing 2 µg/ml polybrene. The cells were washed in media and resuspended at a concentration of $4 \times 10^6$/ml in media. Sera to be tested were heat inactivated at 56° C. for 30 min. and filter sterilized. For each assay 20 ul of virus suspension and 20 µl of a 1:10 dilution of serum was mixed and incubated in a well of a microtiter plate for 1 hr at 4° C. and then 15 min. at room temperature. H9 cells (10 µl) were added to each well and incubation was continued for 1 hr at 37° C. Aliquots (15 µl) of each mixture were plated into 200 µl media in duplicate wells of another microtiter plate. Cultures were incubated at 37° C. in a 5% $CO_2$ incubator. After 3 days, cultures in individual wells were removed, washed 2 times with phosphate buffered saline (PBS) and once with PBS:water, 1:1. Cells were suspended in approximately 30 µl of the same solution and 5 to 10 µl aliquots were spotted on 8-well toxoplasmosis slides for an indirect fixed-cell immune fluorescent assay using a monoclonal antibody to HTLV-III p24.

Sera exhibiting neutralizing antibody activity at a 1:10 dilution were subsequently serially diluted and the assay was repeated to determine antibody titer.

In the following claims and in the specification sera refers to sera containing a substantial quantity of anti-HTLV-III. This includes sera from adult and pediatric AIDS and ARC patients and healthy homosexual (see Table 2). The geometric mean titer ranges from about 44 to 210.

We claim:

1. A method for determining, in samples of human sera, the activity of antibodies which neutralize the infectivity of Human T-Cell Leukemia Virus Type III particles, which method comprises
   (1) heat inactivating and sterilizing samples of human sera to be tested;
   (2) contacting said samples with suspensions of Human T-Cell Leukemia Virus Type III particles, sufficient to infect between 50% to 80% of cells of the Human T-Cell Leukemia Virus Type III permissive cell line H9 (ATCC CRL 8543) in vitro by 3 days post-infection, for a time and under conditions sufficient to permit binding of antibodies in said samples to said Human T-Cell Leukemia Virus Type III particles;
   (3) incubating said samples and suspensions in the presence of H9 (ATCC CRL 8543) cells in vitro for a time and under conditions sufficient to permit infection of said H9 cells by said Human T-Cell Leukemia Virus Type III particles;
   (4) washing said incubated H9 cells to remove extracellular virus;
   (5) contacting said washed cells with an antibody which specifically binds to Human T-Cell Leukemia Virus Type III for a time and under conditions sufficient to permit binding of said antibody to said washed cells to determine the number of Human T-Cell Leukemia Virus Type III infected H9 cells, wherein a decrease in the number of Human T-Cell Leukemia Virus Type III infected H9 cells, as compared to the number of cells infected with Human T-Cell Leukemia Virus Type III after pre-incubation of said Human T-Cell Leukemia Virus Type III with sera negative for Human T-Cell Leukemia Virus Type III neutralizing antibodies, is indicative of the presence of antibodies which neutralize Human T-Cell Leukemia Virus Type III in the tested samples.

* * * * *